(12) United States Patent
Hymel

(10) Patent No.: US 8,452,544 B2
(45) Date of Patent: May 28, 2013

(54) UTILITY AND METHOD FOR THE APPLICATION OF SIGNAL ADVANCE AMPLIFICATION TO ANALOG WAVEFORM OR SIGNAL DETECTION, ACQUISITION AND PROCESSING

(76) Inventor: Chris M. Hymel, Rosharon, TX (US)

( * ) Notice: Subject to any disclaimer, the term of this patent is extended or adjusted under 35 U.S.C. 154(b) by 0 days.

(21) Appl. No.: 12/045,003

(22) Filed: Mar. 9, 2008

(65) Prior Publication Data

US 2011/0184650 A1 Jul. 28, 2011

Related U.S. Application Data

(60) Provisional application No. 60/893,983, filed on Mar. 9, 2007.

(51) Int. Cl.
*G01R 23/16* (2006.01)
*G01R 25/00* (2006.01)
*G01R 29/02* (2006.01)

(52) U.S. Cl.
USPC .................................. 702/19; 702/79; 702/76

(58) Field of Classification Search
USPC ................. 702/19, 32, 38, 66, 70, 76, 78, 79, 702/109; 333/20, 156, 251
See application file for complete search history.

(56) References Cited

U.S. PATENT DOCUMENTS 5,291,156 A * 3/1994 Arntz ............................. 333/20
2003/0073917 A1* 4/2003 Echauz et al. ................ 600/510

OTHER PUBLICATIONS

M,. Kitano, T Nakanishi, K. Sugiyama; Negative Group Delay and Superluminal Propagation: An Electric Circuit Approach; Feb. 21, 2003; all pages.*
Morgan W. Mitchell, Raymond Y. Chiao; Causality and Negative group delays in a simple bandpass amplifier; Mar. 6, 1999, all pages.*

* cited by examiner

*Primary Examiner* — Michael Nghiem
*Assistant Examiner* — Manuel Rivera Vargas

(57) ABSTRACT

An analog waveform signal detection/data acquisition system that is based on negative group delay for reducing inherent delay in analog waveform or signal detection and acquisition and facilitating earlier than otherwise possible responsive actions to analog waveform data. Signal advance amplification and data conditioning reduces distortion and permits greater temporal advance than previously possible.

18 Claims, 8 Drawing Sheets

Data Acquisition System with Signal Advance

Typical Data Acquisition Black Diagram

*Data Acquisition System with Signal Advance*

Idealized Input vs. Output Waveforms

Negative Group Delay Circuit Block Diagram

Signal Front vs. Group Velocity

Simplified R-C Negative Group Delay Circuit Diagram

Simplified Two-Stage R-L-C Negative Group Delay Circuit Diagram

Example of Gain, Phase and Group Delay Responses vs. Frequency

Signal Advance Cascade Input and Output Response

Parallel Array of Cascaded Signal Advance Circuit Stages

UTILITY AND METHOD FOR THE APPLICATION OF SIGNAL ADVANCE AMPLIFICATION TO ANALOG WAVEFORM OR SIGNAL DETECTION, ACQUISITION AND PROCESSING

CITATION TO PRIORITY APPLICATION

This application claims priority of U.S. Provisional Application, Ser. No. 60/893,983, filed 9 Mar. 2007.

BACKGROUND OF THE INVENTION

1. Field of the Invention

The present invention relates to the acquisition and processing of analog waveforms or signals, and more specifically to novel applications of "Signal Advance" to significantly reduce or eliminate the inherent delay in analog waveform or signal detection and acquisition.

2. Background Information

Instrumentation relies on the detection, acquisition and processing of analog signals or waveforms. The process of acquiring analog signals or waveforms typically involves detection through an analog signal transducer, amplification, conversion (including, but not limited to, analog-to-digital conversion) and subsequent signal processing, which may include spectral decomposition and typically, signal or data output, for display or control purposes.

Signal detection and processing delays are necessarily inherent in the electronic systems performing these functions. These delays adversely impact the subsequent use of the acquired signal or processed data based on the acquired signal or waveform, as the physical phenomenon underlying the generation of the analog signals may continue to vary or subside during the period that the signal is being detected, acquired and processed. Any control or intervention necessarily relies on, and in some cases reinforces, or attempts to intervene in underlying events that have transpired, and control, treatment or intervention may be less effective.

Because of these analog signal processing delays, there is no reliable way for any response output to control, intervene, treat or respond through constructive or destructive interference with the underlying phenomenon directly. In essence, any such response is to something that, quite literally, is already complete and in the past.

Current instrumentation used in these control, interventional, therapeutic or other related applications typically act to adjust response output parameters based on extrapolations made from recently acquired data. However, this instrumentation remains unable to reliably instigate a true, real-time response, as there is no way to control the timing of the applied stimulation signal to ensure the appropriately-needed constructive or destructive interference with the phenomenon underlying the generation of the detected analog signal or waveform. Analog signal or waveform conversion speed, which is critical to effective response intervention treatment or control in general, could be greatly improved by the early or "pre-" detection of these analog signals or by elimination or significant reduction of the analog signal or waveform detection and processing delays. The application of "Signal Advance" amplification to the detection of analog signals or waveforms could significantly enhance system response time.

A number of patents and patent applications, as well as, scientific publications discuss Negative Group Delay ("NGD").

U.S. Pat. No. 5,291,156, issued to Arntz on Mar. 1, 1994, is entitled "Method and apparatus for imparting positive phase slope to a narrowband signal." It describes a method and apparatus for imparting a positive phase slope (i.e., a negative group delay) to narrowband signals: it adjusts the phases of the various frequency components of a signal in a manner opposite to that of a delay line. The invention also permits the amount of phase slope to be adjusted, electronically, without the need for electro-mechanical apparatus or the interchange of cables. The amount of phase slope imparted to the signal can be adjusted by varying the gain (or attenuation) of the respective gain control blocks. As such, the '156 patent relates to the separation of a signal into two paths. The first one has a positive delay and thus a negative phase slope. The second is a parallel path and uses negative group delay circuitry to impart a positive phase shift, which can compensate for the positive delay of the first path.

U.S. Patent Application No. 20050127996, published for Jelonnek et al. on Jun. 16, 2005, is entitled "Arrangement for reducing non-linear distortions in an output signal of an amplifier stage." This patent application describes a system for the reduction of non-linear signal distortion, which incorporates a negative group delay transmission device to compensate for transmission delay associated with signal distortion detection in order to generate an error signal that is added to the original signal to reduce the distortion in the original signal via a parallel signal pathway for the signal distortion. This patent application describes a system for distortion reduction related to amplification based on the "Feed-Forward principle". It is used to reduce delays associated with the conversation of analog signals to digital signals using a predictive negative delay amplifier stage in the original signal detection/transmission path via the use of a negative group delay device in a parallel signal path which is later recombined with the original signal propagating through the main signal pathway.

Other references, e.g., U.S. Pat. No. 6,456,950 entitled "Method and apparatus for estimating and digitizing instantaneous frequency and phase of bandpass signals" and U.S. Pat. No. 6,587,064 entitled "Signal processor with local signal behavior and predictive capability", may incorporate early or "predictive" information about the input signal characteristics, but none incorporates a "Signal Advance" amplifier.

Other seemingly-related patents (e.g., U.S. Pat. Nos. 6,466, 604, 6,222,673, 6,081,379 and 4,853,933) relate to the negative group delay phenomenon applied to lasers and characteristics of varying configurations of radiation generating cavities. However, they have no relationship to the application described in the present invention, which applies the negative group delay phenomenon by using operational amplifier-based "Signal Advance" amplification to analog signal/waveform detection and processing in spectral ranges well below those described the aforementioned patents.

Also, other seemingly-related patents (e.g., U.S. Pat. Nos. 5,945,861 and 6,154,079) relate to the use of a negative delay circuit to offset delays in clock signals and prevention of a multi-locking phenomenon related to such clock cycles. However, these applications involve clock pulses and not generalized analog signals and act to offset clock signal delays and not to temporally advance analog signal/waveform detection. Therefore, these groups of patents and similar ones have no relationship to the application of negative delay amplification to an electro-physiological interface to enhance signal detection/processing response, as in the repent invention.

While these earlier teachings may fulfill their respective, particular objectives and requirements, no one has to date proposed an analog signal or waveform detection, acquisition and processing system that provides advance or "early detection" of incoming analog waveform peaks and propagates the waveform to the data acquisition system in advance of the complete detection of the actual incoming signal or waveform.

SUMMARY OF THE INVENTION

In view of the preceding, it is an object of the present invention to advance the field of analog signal detection and response.

It is another object of this present invention to provide an analog waveform signal detection/data acquisition system that incorporates "Signal Advance" amplifier(s) based on the negative group delay phenomenon.

It is another object of this present invention to provide an analog waveform or signal detection/data acquisition system that can significantly improve the performance of instrumentation and devices used for a variety of control, intervention, suppression, reinforcement, enhancement, alarm, treatment or responsive processes that relate to detected analog waveforms or signals.

It is another object of this present invention to provide an analog waveform or signal detection/data acquisition system that can provide a reliable way to investigate or perform reinforcement (negative or positive) between an applied stimulation response or signal and the physiological or other processes underlying the generation of the analog signal or waveform being temporally advanced.

It is another object of this present invention to provide an analog waveform or signal detection/data acquisition system that can reliably instigate a true, real-time response by controlling the timing of the applied stimulation signal or other response output to insure real-time constructive or destructive interference with the actual process underlying the generation of the detected analog waveform or signal including, but not limited to, actual physiological responses.

It is another object of this present invention to provide an analog waveform signal detection/data acquisition system that can significantly enhance a range of electrophysiological and neuro-therapeutic applications, such as EMG, EKG, myelogram, EEG-controlled stimulation, neurofeedback (active or passive) and other neuro-therapy.

It is another object of this present invention to provide an analog waveform signal detection/data acquisition system that can provide new research tools to investigate mechanisms underlying analog signal or waveform generation, including a wide range of physiological and electrophysiological mechanisms.

It is another object of this present invention to provide an analog waveform signal detection/data acquisition system that can enhance the response time and performance of brain-computer interfaces.

It is another object of this present invention to provide an analog waveform signal detection/data acquisition system that can generate significant and useable temporal signal advance for analog signals or waveforms with spectral content typical of electrophysiological signals or waveforms.

It is another object of this present invention to provide an analog waveform signal detection/data acquisition system that can generate significant and useable temporal signal advance for analog signals or waveforms for a wide range of transduced analog signals or waveforms representing a physical measurement for interventional or control purposes.

It is another object of this present invention to provide an analog waveform signal detection/data acquisition system that can generate significant and useable temporal signal advance for analog signals or waveforms for a wide range of analog signals or waveforms to control system(s) that generate analog signals which can be applied to various processes.

It is another object of this present invention to provide an analog waveform signal detection/data acquisition system that can generate significant and useable temporal signal advance for analog signals in which a change in signal or waveform amplitude represents a binary state transition from either a "true" to "false" or "false" to "true" state.

In satisfaction of these and related object, the present invention teaches a unique implementation and use of negative group delay band-pass amplification. Its preferred embodiment is applied to analog waveform signal detection, acquisition and processing. The analog waveform signal detection/data acquisition system incorporates negative group delay band-pass amplification in analog waveform signal detection, acquisition and processing. The result is a significant and useable signal advance for analog waveform signals, especially those with a spectral content in the low end of the spectrum. This useable signal advance will at least reduce if not eliminate signal processing delays and thus, has broad control system, scientific, medical and research applications.

DETAILED DESCRIPTION OF THE PREFERRED EMBODIMENT

Figure 1:
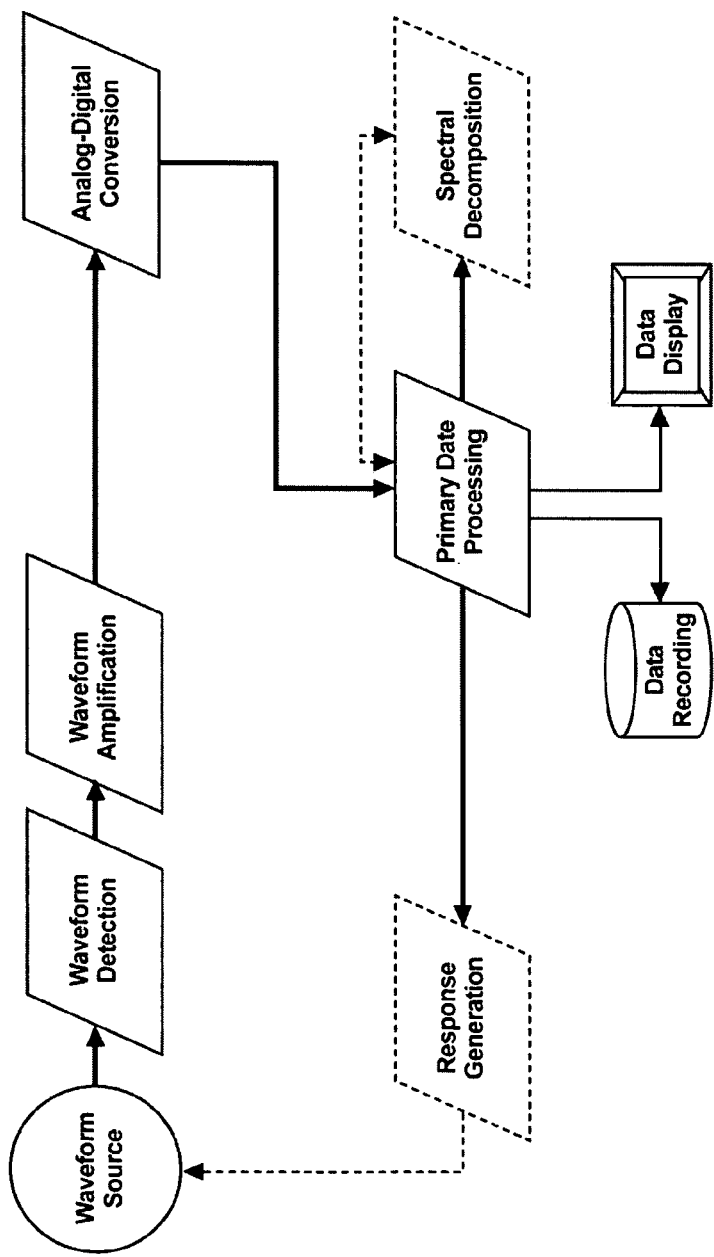
FIG. 1 generally describes the process of acquiring analog signals or waveforms, which typically involves detection through an analog signal transducer, amplification, conversion (including, but not limited to, analog-to-digital conversion) and subsequent signal processing. It may include spectral decomposition and typically, signal or data output, for display or control purposes.

Modern instrumentation relies on detection, acquisition and processing of analog signals (FIG. 1). The performance of the technology used to acquire and process these signals has improved drastically over the last twenty years, but despite these improvements, current systems necessarily have inherent delays, albeit slight (some on the order of microseconds), between the actual generation of analog waveforms to be detected and the ability to react to the acquired data.

Figure 3:
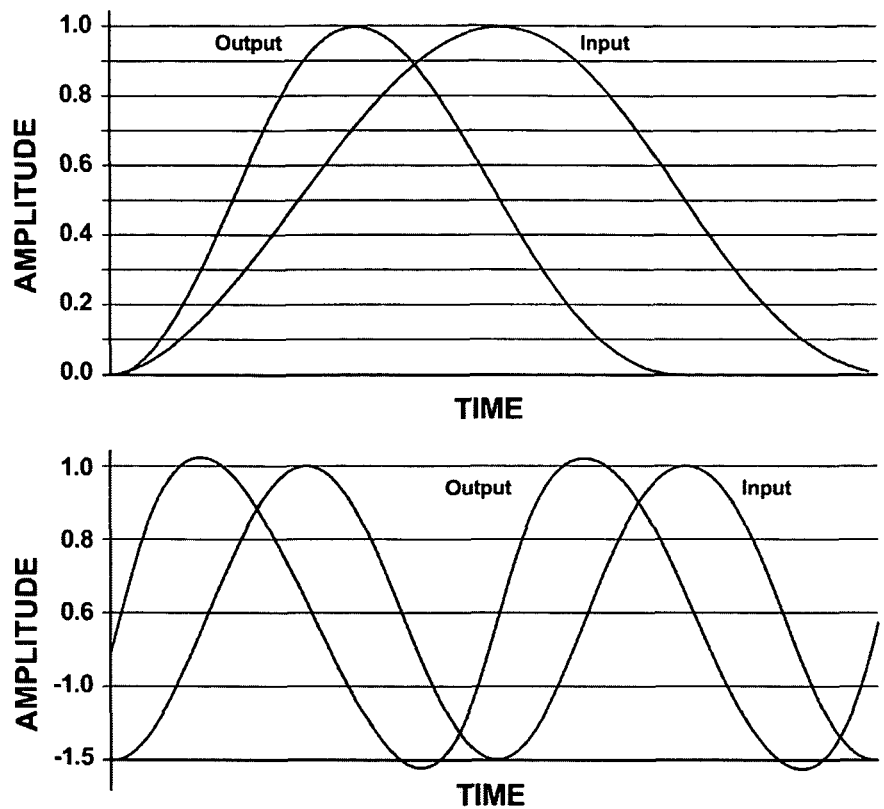
FIG. 3 depicts the relationship of the output to the input of a simple electronic circuit using a Gaussian pulse and sinusoid as input waveforms in which the output waveform peaks precede those of the inputs.
Figure 4:
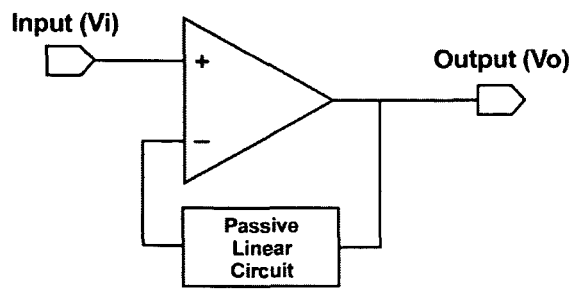
FIG. 4 illustrates the simplest form of such an operational amplifier circuit that exhibits this counter-intuitive response consists of a single stage operational amplifier with a passive linear feedback loop comprised of resistive, capacitive and/or inductive components.
Figure 5:
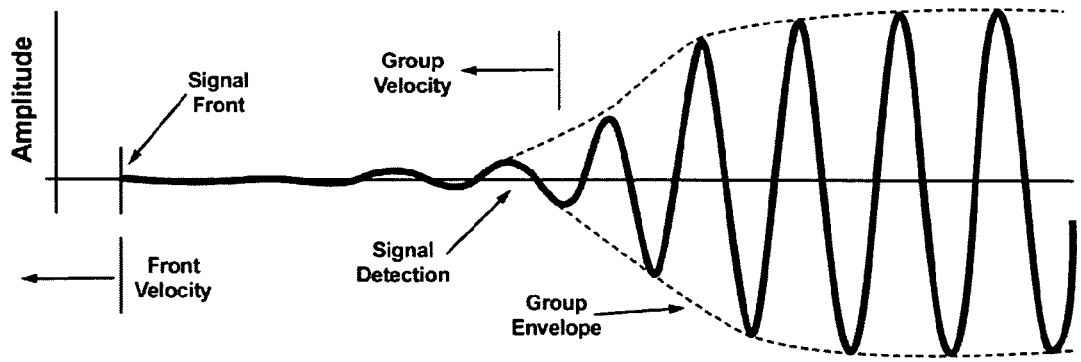
FIG. 5 illustrates group velocity, i.e., the speed of a pulse/waveform.

In recent years, a negative group delay (NGD) phenomenon has been demonstrated in relatively simple electronic circuits, and shown to temporally advance Gaussian pulses, sinusoidal waveforms and complex analog waveforms comprised of multiple superposed sinusoidal components. FIG. 3 depicts the relationship of the output to the input of just such a circuit using a Gaussian pulse and sinusoid as input waveforms in which the output waveform peaks precede those of the inputs. Note the distortion of the output waveform relative to the input in which the output is slightly "skewed" to the left indicating the introduction of higher frequency elements. Over a limited spectral band, the distortion is negligible and linear, facilitating algorithmic removal of distortion digitally for applications in which the advanced analog signal must faithfully reflect the characteristics input signal.

The simplest form of such an operational amplifier circuit that exhibits this counter-intuitive response consists of a single stage operational amplifier with a passive linear feedback loop comprised of resistive, capacitive and/or inductive components.

Typically, an electromagnetic signal or waveform passing through a passive linear circuit will exhibit a positive delay. However, high-gain operational amplifiers act to minimize differences between signals applied to the inverting (−) and non-inverting (+) inputs. In order to satisfy this functional requirement, the operational amplifier supplies a signal with a negative group delay at its output to offset the positive group delay from the passive linear circuit applied to the inverting (−) input. Thus, the negative feedback circuit generates an output pulse whose peak exits the output of the circuit before the peak of the input pulse arrives at the input.

Operational amplifier configurations, which invert transfer functions, are not without precedent. Negative-impedance converters function to cause a resistive load to behave like a negative load. A gyrator circuit inverts impedance such that capacitance behaves like inductance.

At first glance, the behaviour of these circuits appears to contradict the laws of physics as the results suggest that the advanced signal propagation is super-luminal. However, electromagnetic propagation is actually characterized by five different velocities: front velocity (speed of an abrupt signal discontinuity, e.g., a signal suddenly turned on or off); group velocity (speed of a pulse/waveform), phase velocity, velocity of energy transport and, finally, a presumed signal velocity. While the front velocity cannot exceed the speed of light, " . . . the group velocity . . . can be greater than the velocity of light c, can be infinite and even negative!" [Brillouin L, Wave Propagation and Group Velocity, Academic Press, NY, 1960]. As such, the detection of an electromagnetic pulse or wave-form at the output can precede detection at the input. During the time interval between the signal front and the detection of group waveform, electromagnetic energy begins to propagate through the circuit. However, these initial perturbations are not detectable until the oscillations achieve sufficient magnitude. There exists, however, sufficient information in the early portion of any analog waveform to reproduce a temporally advanced waveform using a high-gain operational amplifier.

Thus, the output of an electromagnetic waveform (the group velocity) can be advanced relative to the input—but it cannot exceed the front velocity and thus establishes a theoretical upper limit for a group velocity advance. Further, the question of "superluminality" has been addressed in a number of experiments in which the input signal was discontinued abruptly resulting in a simultaneous (not advanced) discontinuity or signal abruption in the "advanced" output waveform, which demonstrates the causal relationship between the input and advanced output waveforms.

Figure 6:
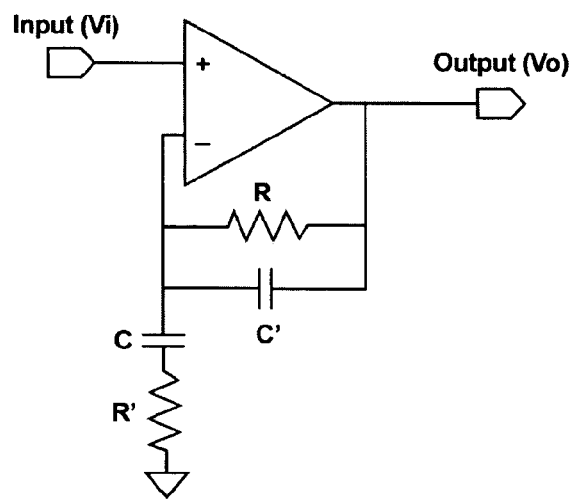
FIG. 6 illustrates a simple circuit consisting of an operational amplifier, two resisters and two capacitors, which exhibits negative group delay properties over a specific spectral band (frequencies well below the amplifier's characteristic frequency).

A simple circuit consisting of an operational amplifier, two resisters and two capacitors, which exhibits negative group delay properties over a specific spectral band (frequencies well below the amplifier's characteristic frequency), is shown in FIG. 6. For this circuit, the transfer function (Tω) defined as the output signal/input signal is defined as follows:

$$T(\omega) = \tilde{V}out/\tilde{V}in = (1 + Z_R/Z_c) = 1 + \frac{i\omega T}{(1+i\omega aT)(1+i\omega bT)}$$

where T=CR, a=C'/C, b=R'/R

Figure 7:
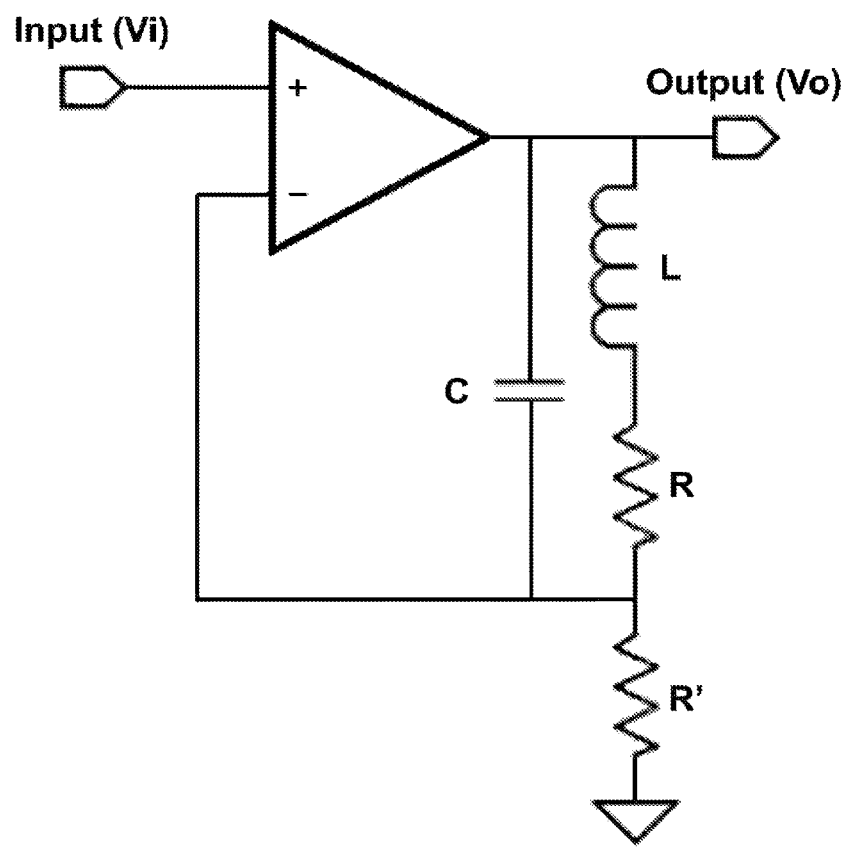
FIG. 7 illustrates the "Signal Advance" amplifier circuit, which includes inductive, resistive and capacitive components.

The "Signal Advance" amplifier circuit shown in FIG. 7 includes inductive as well as resistive and capacitive components. Circuit analysis yields the following a transfer function:

$$T(\omega) = 1 + \frac{1}{R'} \cdot \frac{1}{(R-i\omega L)^{-1} - i\omega C}$$

Figure 8:
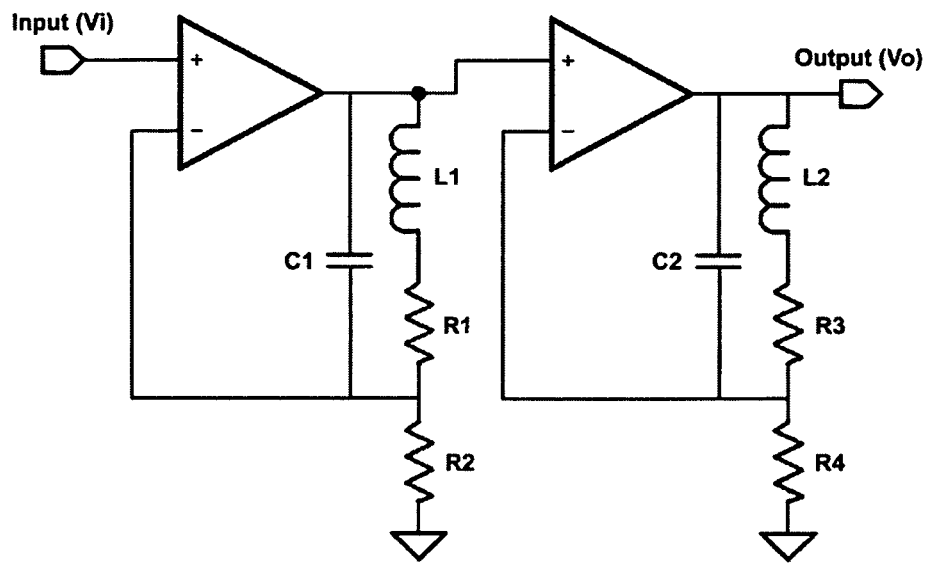
FIG. 8 illustrates a circuit similar to the previous circuit of FIG. 7 and is cascaded with each stage exhibiting different transfer function due to the use of different resistor, capacitor and inductor values. With specific component selection, this multi-stage "Signal Advance" amplifier exhibits a relatively constant advance over a wider spectral range.

A circuit similar to the previous circuit was cascaded (FIG. 8) with each stage exhibiting different transfer function due to the use of different resistor, capacitor and inductor values. By varying the these components values, the multi-stage "Signal Advance" amplifier can exhibit a relatively constant advance of the spectral range of interest for a particular application. The transfer function is expressed as:

$$T(\omega) = \left[1 + \left(\frac{1}{R_1}\right)\left(\frac{1}{(R_1 - i\omega L_1)^{-1} - i\omega C_1}\right)\right] \times$$
$$\left[1 + \left(\frac{1}{R_4}\right)\left(\frac{1}{(R_3 - i\omega L_2)^{-1} - i\omega C_2}\right)\right]$$

The phase associated with these transfer functions is given by:

$$\psi(\omega) = arg[T(\omega)]$$

Circuit analyses for the exemplar "Signal Advance" amplifier circuits described above reveal spectral bands which exhibit negative group delay for a frequency band adjacent to the characteristic or resonant frequency of the circuit. It is within this negative delay spectral band that the circuit(s) generates an analog signal advance.

Figure 9:
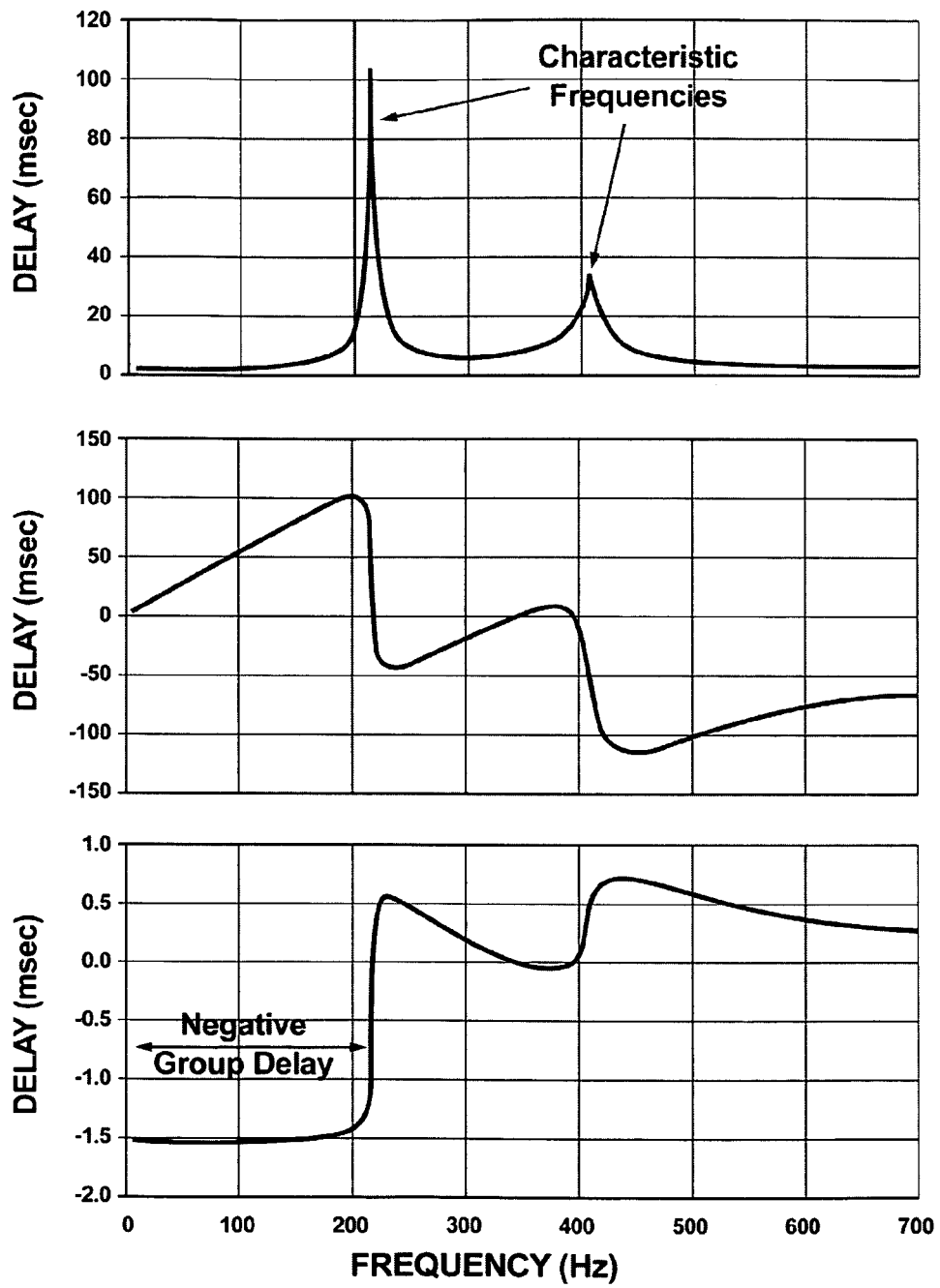
FIG. 9 depicts Gain, Phase and Group Delay characteristics of a signal advance amplifier in which the negative group delay is relatively constant over a specific spectral range. The top graph depicts the gain of the amplifier relative to frequency. Note that the gain is relatively constant up to 200 Hz, a spectral band which is less than, and adjacent to the lower of the two characteristic frequencies of the amplifier circuit. The middle graph (phase vs. frequency) indicates both a positive and relatively linear phase response up to approximately 200 Hz. The third graph depicts the group delay relative to frequency. Group delay is defined as the negative of the rate of change of phase relative to frequency and is expressed mathematically as: $[T(\omega)=-\delta\psi(\omega)/\delta\omega]$ (in the units of time).

FIG. 9 depicts Gain, Phase and Group Delay characteristics of a signal advance amplifier in which the negative group delay is relatively constant over a specific spectral range. The top graph depicts the gain of the amplifier relative to frequency. The gain is relatively constant up to 200 Hz, a spectral band which is less than, and adjacent to the lower of the two characteristic frequencies of the amplifier circuit. The middle graph (phase vs. frequency) indicates both a positive and relatively linear phase response up to approximately 200 Hz. The third graph depicts the group delay relative to frequency. Group delay is defined as the negative of the rate of change of phase relative to frequency and is expressed mathematically as: $[T(\omega) = -\delta\psi(\omega)/\delta\omega]$ (in the units of time). Again, the slope of the phase delay is positive and relatively linear; thus, its derivative is negative and constant in the spectral range less than 200 Hz.

Based on the detailed analyses of the exemplar negative delay circuits detailed above, the amount of negative delay, or signal advance, which can be achieved, is indirectly related to the spectral content or frequency of the analog waveform to which it is applied, i.e., a larger negative delay or signal advance is possible for lower frequency signals.

Note that the use of the inductive component in the negative group delay circuits facilitates signal advance for a complex analog signal over a wider spectral band. As described previously, larger analog signal advances are indirectly proportional to the spectral content of the analog waveform. To achieve a lower characteristic or resonant frequency in a "Signal Advance" amplifier circuit may require both a large capacitance and inductance as the resonant frequency ($\omega_r$) is approximated by:

$$\omega_r \approx 1/\sqrt{LC}.$$

Inductors are typically measured in units of milli-henries (mH) or lower. Thus, a gyrator may be used to simulate large inductance values (measured in Henries (H)).

For a number of applications and, in particular, biomedical interventional applications such as electrophysiology, the temporally advanced output may need to be a high fidelity representation of the original input waveform. In these applications, the analog waveforms being advanced are typically in the lower frequency range (hundreds of Hertz). Thus, compensation for the inherent signal distortion can be accomplished through the use of digital signal processors which operate at conversion rates that are negligible with respect to the duration of waveform advance achieved. A number of analog-to-digital (A-D) converters and digital signal processors, which can be used to perform digital filtering and signal reconstruction, have response times ranging from just under 100 to over 1,000 times less than the expected waveform advance.

Figure 10:
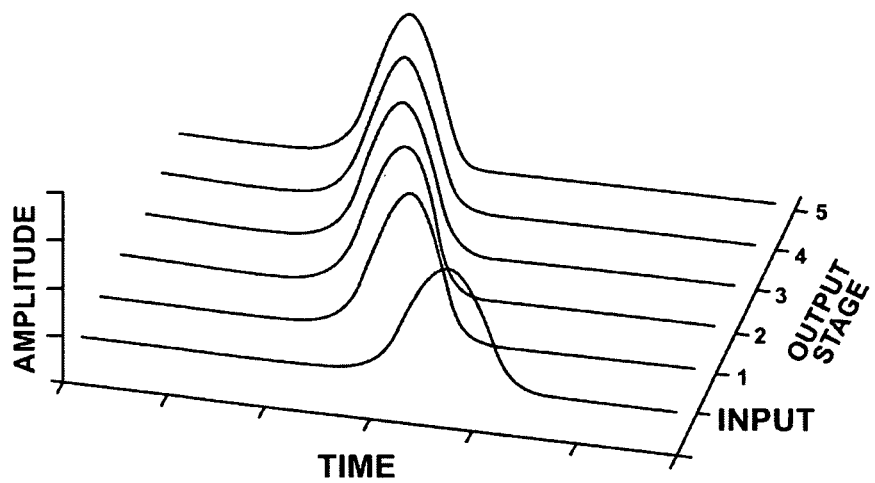
FIG. 10 illustrates how the duration of the waveform advance can be increased (in a limited fashion due to concomitant, but acceptable, signal distortion) by cascading multiple negative group delay amplifier stages over a limited spectral range.

The duration of the waveform advance can be increased (in a limited fashion due to concomitant, but acceptable, signal distortion) by cascading multiple negative group delay amplifier stages over a limited spectral range (FIG. 10). By cascading multiple "Signal Advance" Amplifier stages, a waveform advance could exceed the input pulse width, but the maximum advance may be limited to a few pulse rise-times due to the increase in signal distortion in each stage and the theoretical front velocity limit.

Figure 2:
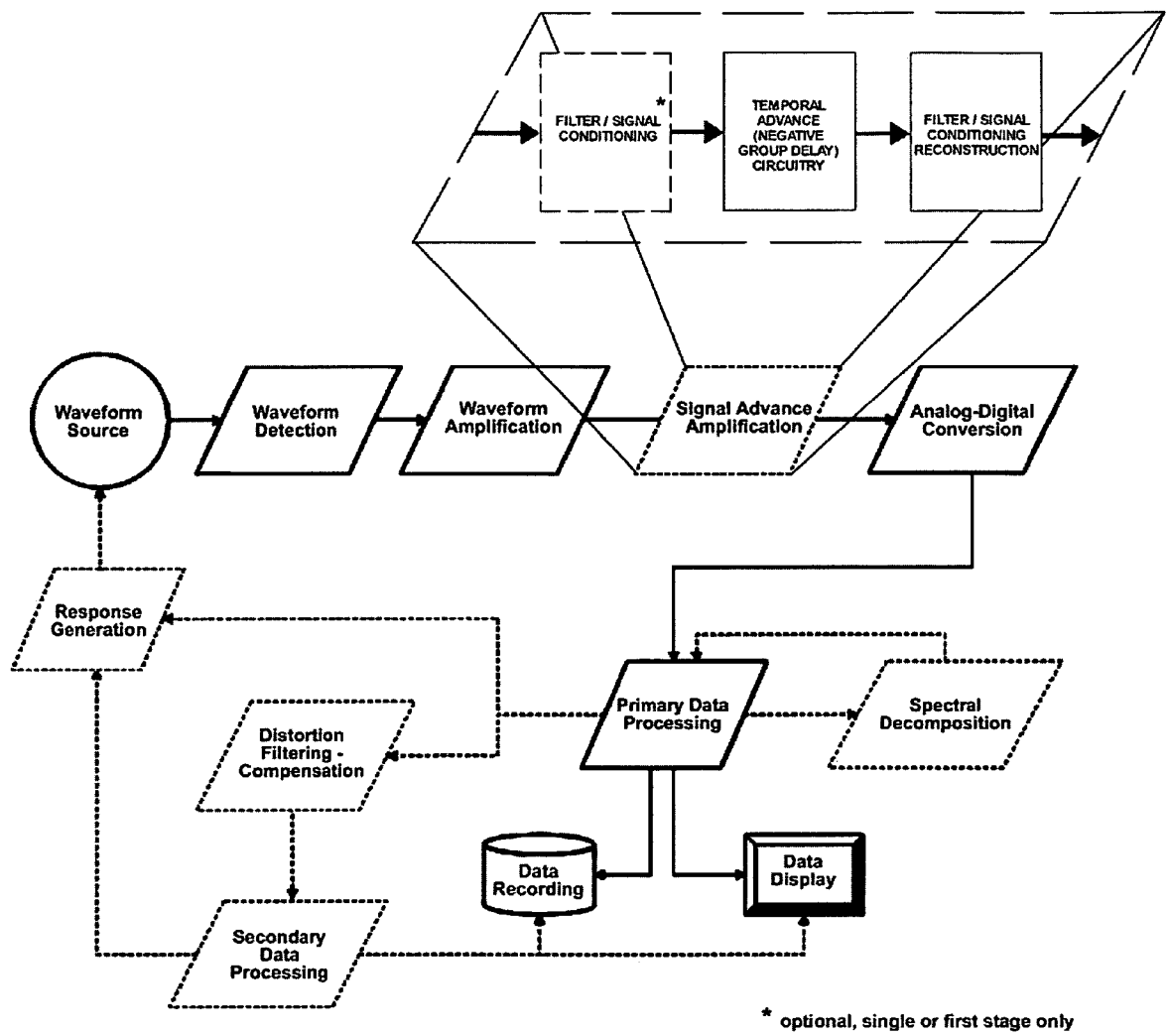
FIG. 2 generally depicts the application of "Signal Advance" amplification to the detection of analog signals or waveforms. The inset figure depicts the elements which comprise the signal advance means comprised of negative group delay (temporal advance) and signal filtering conditioning reconstruction stages.
Figure 11:
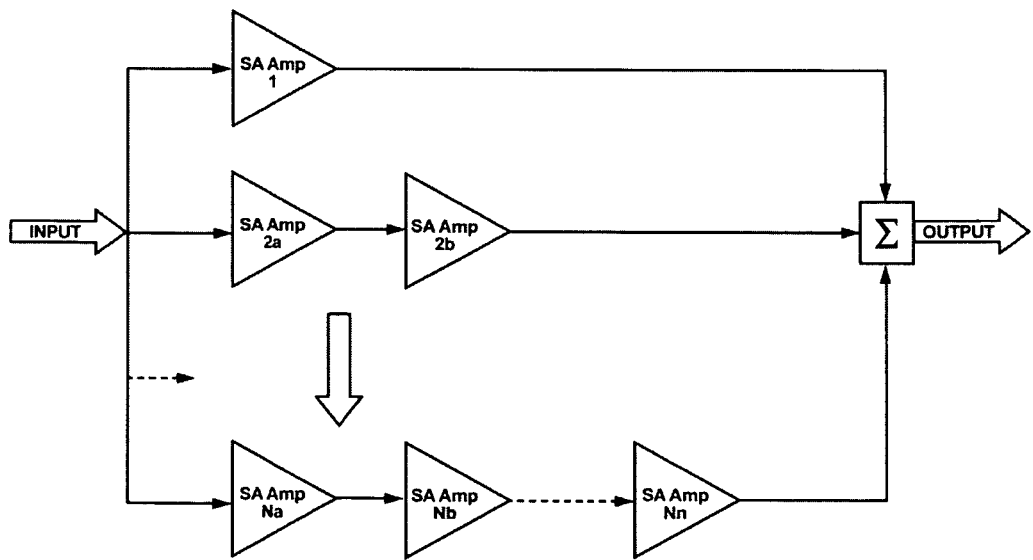
FIG. 11 illustrates parallel arrays of narrower spectral band "Signal Advance" amplifiers, in which some of the bands the "Signal Advance" amplifiers are cascaded. This parallel array of amplifiers can be configured to generate a more linear input-output response, which in turn can yield a temporal advance of signals over particular spectral ranges of interest.

As discussed previously, digital filtering and signal reconstruction (FIG. 2) can be applied to reduce or eliminate the waveform or signal distortion in a fraction of the duration of the temporal waveform advance achieved. Reduction or elimination of higher frequency distortion resulting from "Signal Advance" amplification, which approaches the characteristic or resonant frequency of the circuit, is particularly useful when successive amplifier stages are cascaded to achieve increased duration of the temporal waveform or signal advance Parallel arrays of narrower spectral band "Signal Advance" amplifiers, in which some of the bands the "Signal Advance" amplifiers are cascaded (FIG. 11), can be configured to generate a more linear input-output response. This provides a mechanism to achieve a temporal advance of signals or waveforms over particular spectral ranges of interest as narrower spectral band can be tuned to detect specific aspects of the incoming analog signal or waveform through the use of just such a cascade arrangement.

As such, for a wide range of instrumentation used in analog signal or waveform detection, acquisition and processing, an approach utilizing "Signal Advance" amplification holds the promise of significantly enhancing a range of control and biomedical applications.

A primary consideration in practical application of "Signal Advance" amplification to analog signal detection, acquisition and processing is to achieve a sufficient signal advance to allow for a usable response. Therefore, design of a practical "Signal Advance" amplifier necessarily begins with a detailed analysis of the analog waveform to be advanced in order to determine the waveform characteristics for which circuitry must be designed. The amplifier design must take in account waveform characteristics which include the frequency range, pulse widths (or durations) comprising the signal, pulse shape, etc.

The second consideration is, after determining the signal advance which can be achieved, is to determine the potential to produce a useable response based on the duration of the temporal advance obtained. It may be necessary to cascade multiple stages or to detect different aspects of the analog waveform using parallel "Signal Advance" paths. It is the ability to provide a useable response given the availability of advanced signal or waveform detection that is the key to practical application of this technology.

For some potential applications of the present invention, signal distortion is of little or no consequence. One example is the detection of an analog pulse in which the difference in amplitude, or simply the existence of a pulse, represents a change in a binary state, a threshold condition, or other true/false transition. In ECG/EKG (Electro-Cardiograph) waveform detection, a slightly distorted PQRST waveform may still be acceptable for the detection of abnormal wave patterns as long as the signals distortions resulting from "Signal Advance" amplification are consistent. Other applications, such as neurofeedback, may require or benefit from the removal of, or compensation for, the signal distortion, as it is the spectral content that may be important to the therapeutic application.

In order to develop a mechanism for compensating the distortion which results from "Signal Advance" amplification, the resultant distortions arising in the temporally advanced analog signal or waveforms must be characterized for the particular spectral range and at a resolution appropriate for the analog waveforms being detected. In order to generate data that can be used to devise methodologies and algorithms for reconstituting the spectral content of the original analog input signal or waveform, signal generation and data acquisition systems, which provide synchronized high sample-rate and wide bandwidth simultaneous data sampling and signal generation capacity are used to generate high fidelity analog input signal and acquire the temporally advanced analog output signals or waveforms. Spectral decomposition of both the input and output signals are obtained by applying fast Fourier Transform (FFT) analyses to the input and output signals from each "Signal Advance" amplifier stage. The comparison of the spectral content of the respective signals provides data to characterize and digitally reconstitute the spectral content of the original analog input waveform.

As the distortion is minimal and consistent across the design spectral band, empirically-obtained data, as described above, can be used to characterize the distortion and devise methods for subsequent removal of the distortion digitally for a particular application. For example, a simple "look-up" table could be incorporated into embedded hardware that replaces the spectrally decomposed components of the advanced signals or waveforms with the equivalent amplitude and frequency data for the original input signal.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method to temporally advance the detection and characterization of analog data, comprising the steps of:
    interfacing an analog data detector with a signal advance means comprising a negative group delay (NGD) circuit means having a NGD signal output means for producing temporally advanced raw indicia of analog data received by said analog data detection means;
    determining analog wave form characteristics of said analog data, said analog wave form characteristics comprising a range of frequencies, pulse widths, pulse shape and phase slope relative to said frequency range;
    determining a response based on said wave form characteristics and duration of the temporally advanced raw indicia of the analog data received;
    said NGD signal output means interfaced with signal filtering and reconstruction means for producing corrected indicia that more accurately represent said analog data detected by said analog data detection means than said temporally advanced raw indicia;
    wherein the gain, the duration of temporal advance or both the gain and duration of temporal advance of said corrected indicia, is/are relatively constant over a specified frequency spectrum for signals with a wide spectral range.

2. The method of claim 1 wherein said analog data detector is a medical monitoring device for detecting and transmitting data indicative of electromagnetic waves produced by organs and systems of the human body.

3. The method of claim 1, further comprising: a plurality of signal advance means, wherein the signal advance means is interfaced in parallel to an analog data detector to produce two or more temporally advanced and corrected raw indicia.

4. The method of claim 1, further comprising: interfacing the analog data detector in parallel to one or more signal advance means to produce two or more temporally advanced and corrected raw indicia.

5. The method of claim 1, further comprising: interfacing the analog data detector in parallel to one or more of serially cascaded signal advance means to produce two or more temporally advanced and corrected indicia.

6. A signal advance device to temporally advance the detection and characterization of analog data, comprising:
    interfacing an analog data detector with a signal advance device comprising a NGD circuit means having an NGD signal output means for producing temporally advanced raw indicia of analog data received by said analog data detection means;
    determining analog wave form characteristics of said analog data, said analog wave form characteristics comprising a range of frequencies, pulse widths, pulse shape and phase slope relative to said frequency range;
    determining a response based on said wave form characteristics and duration of the temporally advanced raw indicia of the analog data received;
    said NGD signal output means interfaced with signal filtering and reconstruction means for producing corrected indicia that more accurately represent said analog data detected by said analog data detection means than said temporally advanced raw indicia;
    wherein the gain, the duration of temporal advance or both the gain and duration of temporal advance of said corrected indicia, is/are relatively constant over a specified frequency spectrum for signals with a wide spectral range.

7. The device of claim 6, wherein said analog data detector is a medical monitoring device for detecting and transmitting data indicative of electromagnetic waves produced by organs and systems of the human body.

8. The device of claim 6, further comprising: a plurality of signal advance devices, wherein the signal advance devices are interfaced in parallel to an analog data detector to produce two or more temporally advanced and corrected raw indicia.

9. The device of claim 6, further comprising: interfacing the analog data detector in parallel to one or more signal advance devices to produce two or more temporally advanced and corrected raw indicia.

10. The device of claim 6, further comprising: interfacing the analog data detector in parallel to one or more serially cascaded signal advance devices to produce two or more temporally advanced and corrected raw indicia.

11. A method to temporally advance the detection and characterization of analog data, comprising the steps of:
    interfacing an analog data detector with a plurality of serially cascaded signal advance means, each of said signal advance means comprising a negative group delay (NGD) circuit means having a NGD signal output means for producing temporally advanced raw indicia of analog data received by said analog data detection means;

determining analog wave form characteristics of said analog data, said analog wave form characteristics comprising a range of frequencies, range, pulse widths, pulse shape and phase slope relative to said frequency range;

determining a response based on said wave form characteristics and duration of the temporally advanced raw indicia of the analog data received;

said NGD signal output means interfaced with a signal filtering and reconstruction means for producing corrected indicia that more accurately represent said analog data detected by said analog data detection means than said temporally advanced raw indicia;

wherein the gain, the duration of temporal advance or both the gain and duration of temporal advance of said corrected indicia, is/are relatively constant over a specified frequency spectrum for signals with a wide spectral range.

12. The method of claim 11, wherein said analog data detector is a medical monitoring device for detecting and transmitting data indicative of electromagnetic waves produced by organs and systems of the human body.

13. The method of claim 11, wherein each of the plurality of serially cascaded signal advance means outputs temporally advanced and corrected indicia.

14. The method of claim 11, wherein the serially cascaded signal advance means is interfaced in parallel to a plurality of signal advance means, and each signal advance means is interfaced in parallel to an analog data detector to produce two or more temporally advanced and corrected raw indicia.

15. A signal advance device to temporally advance the detection and characterization of analog data comprising:

interfacing an analog data detector with a plurality of serially cascaded signal advance means each of which said signal advance means comprising a NGD circuit means having an NGD signal output means for producing temporally advanced raw indicia of analog data received by said analog data detection means;

determining analog wave form characteristics of said analog data, said analog wave form characteristics comprising a range of frequencies, pulse widths, pulse shape and phase slope relative to said frequency range;

determining a response based on said wave form characteristics and duration of the temporally advanced raw indicia of the analog data received;

said NGD signal output means being interfaced with signal filtering and reconstruction means for producing corrected indicia that more accurately represent said analog data detected by said analog data detection means than said temporally advanced raw indicia;

wherein the gain, the duration of temporal advance or both the gain and duration of temporal advance of said corrected indicia, is/are relatively constant over a specified frequency spectrum for signals with a wide spectral range.

16. The device of claim 15, wherein said analog data detector is a medical monitoring device for detecting and transmitting data indicative of electromagnetic waves produced by organs and systems of the human body.

17. The device of claim 15, wherein each of the plurality of the serially cascaded signal advance means outputs a temporally advanced and corrected indicia.

18. The device of claim 15, wherein the serially cascaded signal advance means are interfaced in parallel to an analog data detector to produce two or more temporally advanced and corrected raw indicia.

* * * * *